US012623087B2

(12) United States Patent
Talebinejad et al.

(10) Patent No.: US 12,623,087 B2
(45) Date of Patent: May 12, 2026

(54) METHOD FOR GENERATING UNIDIRECTIONAL MONOPHASIC PULSE AND USE OF SUCH PULSE

(71) Applicant: NeuroQore, Inc., San Francisco, CA (US)

(72) Inventors: Mehran Talebinejad, San Francisco, CA (US); Adrian Chan, San Francisco, CA (US)

(73) Assignee: NeuroQore, Inc., San Francisco, CA (US)

( * ) Notice: Subject to any disclaimer, the term of this patent is extended or adjusted under 35 U.S.C. 154(b) by 1221 days.

(21) Appl. No.: 17/497,480

(22) Filed: Oct. 8, 2021

(65) Prior Publication Data

US 2023/0111038 A1    Apr. 13, 2023

(51) Int. Cl.
*A61N 2/00*          (2006.01)
*A61N 2/02*          (2006.01)
*H03K 17/567*        (2006.01)

(52) U.S. Cl.
CPC .............. *A61N 2/006* (2013.01); *A61N 2/02* (2013.01); *H03K 17/567* (2013.01)

(58) Field of Classification Search
CPC ......... A61N 2/006; A61N 2/02; H03K 17/567
USPC ..................................... 600/12–15
See application file for complete search history.

(56) References Cited

U.S. PATENT DOCUMENTS 3,290,617 A  *  12/1966  Bellem .................... H03C 3/00
                                                      327/482

3,932,741 A  *   1/1976  Hanson ................... H03K 4/066
                                                      327/133
4,585,951 A  *   4/1986  Wurzburg .............. H03K 4/066
                                                      327/131
2007/0293916 A1*  12/2007  Peterchev ................ A61N 2/02
                                                      607/61
2010/0069704 A1*   3/2010  Peterchev .............. A61N 2/006
                                                      600/14

(Continued)

OTHER PUBLICATIONS

"NeuroQore magnet treatment is effective and hopes in curing depression" by The Silicon Review, Feb. 10, 2017, retrieved online on Jul. 22, 2025 at URL https://thesiliconreview.com/2017/02/neuroqore-magnet-treatment-is-effective-and-hopes-in-curing-depression (Year: 2017).*

(Continued)

*Primary Examiner* — Sunita Reddy
(74) *Attorney, Agent, or Firm* — Bradley Arant Boult Cummings LLP; Henry B. Ward, III

(57) ABSTRACT

Method of generating a unidirectional monophasic triangular pulse using a device having a voltage bank with an adjustable voltage level; use of such a pulse to induce a current flow in an individual's brain. A voltage control device of the device includes one or more switches, such as IGBTs, and/or one or more inductors. Energy from the voltage bank is discharged into a magnetic coil of the device. When the energy in the coil reaches a predetermined peak level, the voltage of the voltage bank is rapidly changed from a first level to a second level, such that the majority of the energy in the coil is recovered while the voltage level is at the second level. In some embodiments, the first level is 5 times the second level. In some embodiments, the second level is 5 times the first level.

8 Claims, 9 Drawing Sheets

(56) References Cited

U.S. PATENT DOCUMENTS

| | | | | |
|---|---|---|---|---|
| 2012/0108883 A1* | 5/2012 | Peterchev | | A61N 2/02 |
| | | | | 600/14 |
| 2015/0246238 A1* | 9/2015 | Moses | | A61N 1/36025 |
| | | | | 600/14 |
| 2016/0213944 A1* | 7/2016 | Talebinejad | | A61N 2/006 |
| 2017/0001026 A1* | 1/2017 | Schwarz | | A61N 2/008 |
| 2020/0101308 A1* | 4/2020 | Ilmoniemi | | A61N 2/02 |

OTHER PUBLICATIONS

Berlim, M. T. et al. Clinically meaningful efficacy and acceptability of low-frequency repetitive transcranial magnetic stimulation (rTMS) for treating primary major depression: a meta-analysis of randomized, double-blind and sham-controlled trials. Neuropsychopharmacol. Off. Publ. Am. Coll. Neuropsychopharmacol. 38, 543-551 (2013).

Magnezi, R. et al. Comparison between neurostimulation techniques repetitive transcranial magnetic stimulation vs electroconvulsive therapy for the treatment of resistant depression: patient preference and cost-effectiveness. Patient Prefer. Adherence 10, 1481-1487 (2016).

Durmaz, O. et al. Repetitive Transcranial Magnetic Stimulation (rTMS)-Induced Trigeminal Autonomic Cephalalgia. Noro Psikiyatr. Ars. 52, 309-311 (2015).

Sobreira, G. et al. Adverse effects in repetitive transcranial magnetic stimulation—prevention and management. Eur. Psychiatry 33, S555-S556 (2016).

Cristancho, M. A., et al. Transcranial magnetic stimulation maintenance as a substitute for maintenance electroconvulsive therapy: a case series. J. ECT 29, 106-108 (2013).

Gutiérrez-Mutoz, A. M. et al. Theta burst stimulation: Technical aspects about TMS devices. Brain Stimul. 13, 562-564 (2020).

Cash, R. F. H. et al. Using Brain Imaging to Improve Spatial Targeting of Transcranial Magnetic Stimulation for Depression. Biol. Psychiatry 1-12 (2020) doi:10.1016/j.biopsych.2020.05.033.

Fox, M. D. et al. Efficacy of transcranial magnetic stimulation targets for depression is related to intrinsic functional connectivity with the subgenual cingulate. Biol. Psychiatry 72, 595-603 (2012).

Kessler, R. C. et al. Lifetime Prevalence and Age-of-Onset Distributions of DSM-IV Disorders in the National Comorbidity Survey Replication. Arch. Gen. Psychiatry 62, 593-602 (2005).

Nestler, E. J. et al. Review Neurobiology of Depression the focus of efforts to understand the pathophysiology. Neuron vol. 34 (2002).

Krishnan, V. & Nestler, E. J. The molecular neurobiology of depression. Nature 455, 894-902 (2008).

Saveanu, R. V. & Nemeroff, C. B. Etiology of Depression: Genetic and Environmental Factors. Psychiatr. Clin. North Am. 35, 51-71 (2012).

McMahon, F. J. Population-based estimates of heritability shed new light on clinical features of major depression. Am. J. Psychiatry 175, 1058-1060 (2018).

Oakes, P. et al. The neuroanatomy of depression: A review. Clin. Anat. (2016).

Richards, D. Prevalence and clinical course of depression: A review. Clin. Psychol. Rev. 31, 1117-1125 (2011).

Wong, M. L. & Licinio, J. Research and treatment approaches to depression. Nat. Rev. Neurosci. 2, 343-351 (2001).

Meyer, J. H. et al. Elevated Monoamine Oxidase A Levels in the Brain: An Explanation for the Monoamine Imbalance of Major Depression. Arch. Gen. Psychiatry 63, 1209-1216 (2006).

Sheline, Y.I. et al. The hippocampus and depression. Eur. Psychiatry 17, 300s-305s (2002).

Rudebeck, P. H. et al. A role for primate subgenual cingulate cortex in sustaining autonomic arousal. Proc. Natl. Acad. Sci. U. S. A. 111, 5391-5396 (2014).

Alexander, L. et al. Over-activation of primate subgenual cingulate cortex enhances the cardiovascular, behavioral and neural responses to threat. Nat. Commun. 11, (2020).

Drevets, W. C. et al. The subgenual anterior cingulate cortex in mood disorders. CNS Spectr. 13, 663-681 (2008).

Li, B. J. et al. A brain network model for depression: From symptom understanding to disease intervention. CNS Neurosci. Ther. 24, 1004-1019 (2018).

Bosma, R. L. et al. Using magnetic resonance imaging to visualize the brain in chronic pain. Pain 158, 1192 (2017).

Liang, X. et al. Topologically Reorganized Connectivity Architecture of Default-Mode, Executive-Control, and Salience Networks across Working Memory Task Loads. Cereb. Cortex 26, 1501-1511 (2016).

Damoiseaux, J. S. et al. Consistent resting-state networks. (2006).

Dichter, G. S. et al. A systematic review of relations between resting-state functional-MRI and treatment response in major depressive disorder. J. Affect. Disord. 172, 8-17 (2015).

American Psychiatric Association. Diagnostic and Statistical Manual of Mental Disorders (DSM-5). (2013).

Thase, M. E. Using biomarkers to predict treatment response in major depressive disorder: Evidence from past and present studies. Dialogues Clin. Neurosci. 16, 539-544 (2014).

Koenig, A. M. & Thase, M. E. First-line pharmacotherapies for depression—What is the best choice? Pol. Arch. Med. Wewn. 119, 478-486 (2009).

Lattimore, K. A. et al. Selective serotonin reuptake inhibitor (SSRI) use during pregnancy and effects on the fetus and newborn: A meta-analysis. J. Perinatol. 25, 595-604 (2005).

Gartlehner, G. et al. Discontinuation rates for selective serotonin reuptake inhibitors and other second-generation antidepressants in outpatients with major depressive disorder: A systematic review and meta-analysis. Int. Clin. Psychopharmacol. 20, 59-69 (2005).

Kavalali, E. T. & Monteggia, L. M. Synaptic mechanisms underlying rapid antidepressant action of ketamine. Am. J. Psychiatry 169, 1150-1156 (2012).

Singh, J. B. et al. Intravenous Esketamine in Adult Treatment-Resistant Depression: A Double-Blind, Double-Randomization, Placebo-Controlled Study. Biol. Psychiatry 80, 424-431 (2016).

Rief, W. et al. Meta-analysis of the placebo response in antidepressant trials. J. Affect. Disord. 118, 1-8 (2009).

Cipriani, A. et al. Comparative efficacy and acceptability of 21 antidepressant drugs for the acute treatment of adults with major depressive disorder: a systematic review and network meta-analysis. Lancet 391, 1357-1366 (2018).

Kirsch, I. et al. Initial severity and antidepressant benefits: A meta-analysis of data submitted to the food and drug administration. PLoS Med. 5, 0260-0268 (2008).

Fava, M. & Davidson, K. G. Definition and Epidemiology of Treatment-Resistant Depression. Psychiatr. Clin. North Am. 19, 179-200 (1996).

Saltiel, P. F. & Silvershein, D. I. Major depressive disorder: Mechanism-based prescribing for personalized medicine. Neuropsychiatr. Dis. Treat. 11, 875-888 (2015).

Gelenberg, A. J. et al. The state of knowledge of chronic depression. J. Clin. Psychiatry 67, 179-184 (2006).

Fregni, F. & Pascual-Leone, A. Technology Insight: Noninvasive brain stimulation in neurology—Perspectives on the therapeutic potential of rTMS and tDCS. Nat. Clin. Pract. Neurol. 3, 383-393 (2007).

Kayser, S. et al. Antidepressant effects, of magnetic seizure therapy and electroconvulsive therapy, in treatment-resistant depression. J. Psychiatr. Res. 45, 569-576 (2011).

Grunhaus, L. et al. A randomized controlled comparison of electroconvulsive therapy and repetitive transcranial magnetic stimulation in severe and resistant nonpsychotic major depression. Biol. Psychiatry 53, 324-331 (2003).

Brodaty, H. et al. 'Side effects' of ECT are mainly depressive phenomena and are independent of age. J. Affect. Disord. 66, 237-245 (2001).

Peterchev, A. V. Electroconvulsive therapy stimulus parameters: Rethinking dosage. J. ECT 26, 159-174 (2010).

Merrill, D. R. et al. Electrical stimulation of excitable tissue: design of efficacious and safe protocols. J. Neurosci. Methods 141, 171-198 (2005).

(56)        References Cited

OTHER PUBLICATIONS

Trevino, K. et al. A review of continuation electroconvulsive therapy: Application, safety, and efficacy. J. ECT 26, 186-195 (2010).

Kellner, C. H. et al. Continuation electroconvulsive therapy vs pharmacotherapy for relapse prevention in major depression: A multisite study from the consortium for research in electroconvulsive therapy (CORE). Arch. Gen. Psychiatry 63, 1337-1344 (2006).

Porter, R. J. et al. Cognitive side-effects of electroconvulsive therapy: what are they, how to monitor them and what to tell patients. BJPsych open 6, e40-e40 (2020).

Lisanby, S. H., et al. The effects of electroconvulsive therapy on memory of autobiographical and public events. Arch. Gen. Psychiatry 57, 581-590 (2000).

Xu, J. et al. Electroconvulsive therapy modulates functional interactions between submodules of the emotion regulation network in major depressive disorder. Transl. Psychiatry 10, (2020).

Wang, D. et al. Functional connectivity underpinnings of electroconvulsive therapy-induced memory impairments in patients with depression. Neuropsychopharmacology 45, 1579-1587 (2020).

Cao, B. et al. Predicting individual responses to the electroconvulsive therapy with hippocampal subfield volumes in major depression disorder. Sci. Rep. 8, 1-8 (2018).

O'Reardon, J. P. et al. Efficacy and Safety of Transcranial Magnetic Stimulation in the Acute Treatment of Major Depression: A Multisite Randomized Controlled Trial. Biol. Psychiatry 62, 1208-1216 (2007).

Goetz, S. M. et al. Enhancement of Neuromodulation with Novel Pulse Shapes Generated by Controllable Pulse Parameter Transcranial Magnetic Stimulation. Brain Stimul. 9, 39-47 (2016).

Johnson, K. A. et al. Prefrontal rTMS for treating depression: location and intensity results from the OPT-TMS multi-site clinical trial. Brain Stimul. 6, 108-117 (2013).

Peleman, K. et al. Using 3D-MRI to localize the dorsolateral prefrontal cortex in TMS research. World J. Biol. Psychiatry 11, 425-430 (2010).

Sparing, R. et al. Transcranial magnetic stimulation and the challenge of coil placement: A comparison of conventional and stereotaxic neuronavigational strategies. Hum. Brain Mapp. 29, 82-96 (2008).

* cited by examiner

METHOD FOR GENERATING UNIDIRECTIONAL MONOPHASIC PULSE AND USE OF SUCH PULSE

TECHNICAL FIELD

The present invention relates to transcranial magnetic stimulation (TMS). More specifically, the present invention relates to a method for generating a unidirectional monophasic pulse and to using such a pulse to induce a current flow in an individual's brain.

BACKGROUND

To better understand the present invention, the reader is directed to the listing of citations at the end of this description. For ease of reference, these citations and references have been referred to by their listing number throughout this document. The contents of the citations in the list at the end of this description are hereby incorporated by reference herein in their entirety.

Depression is the leading cause of disability worldwide according to the World Health Organization [1], with a lifetime prevalence of 10.8% [2]. Symptoms of depression include depressed mood, inability to experience pleasure, irritability and abnormalities in sleep and appetite [3]. Those suffering from depression are at an increased risk of suicide and are more likely to develop other health problems and complications, highlighting the urgent need for effective treatments [4]. Risk factors for depression are both environmental and genetic. Environmental stressors such as early life trauma, abuse, and neglect can dramatically increase the risk of depression [5]. Depression is also transmissible from parents, with some studies reporting that about half of the variability in depression can be explained by genes [6]. Although depression has no single root cause, extensive study of the neuroscience of depression reveals common themes of abnormal anatomy, imbalanced biochemistry, and altered connectivity between brain regions [7]. Psychiatric and pharmacological treatments are considered to be first-line therapies, but many patients are treatment resistant or experience relapse. According to some studies, up to 60% of patients experience relapse within 5 years of treatment [8].

The most common, fundamental cell of the brain is the neuron; the average human brain contains approximately 86 billion neurons. Neurons typically have four main parts: a cell body, an axon, axon terminals, and dendrites. To send a message to another neuron, an electrical signal (called an action potential) is sent down the axon resulting in the release of neurotransmitters, the chemical messengers of the brain, from the axon terminals. Dendrites are the parts of the neuron that typically receive signals from other neurons, with neurotransmitters binding to receptor sites in the dendrites.

At rest, a neuron is negatively charged, meaning the inside of the neuron is electrically negative compared to the space outside the cell. (For convenience, assume that the neuron typically has a resting potential of −70 mV.) Signals from other neurons can excite the neuron (make the neuron less negatively charged) or inhibit the neuron (make the neuron more negatively charged). If the combination of these incoming signals, from other neurons, excites the neuron beyond a critical threshold (for convenience, assume a threshold of −55 mV), an action potential is triggered. The action potential travels from the cell body down an axon to the axon terminal.

Many neural synapses in the brain are comprised of: (1) axon terminals of the presynaptic neuron, which sends information to another neuron by releasing neurotransmitters, (2) neurotransmitter receptor sites in postsynaptic neurons (commonly in the dendrites), which receives information from another neuron, and (3) the synaptic cleft, which is the small space between the axon terminals of the presynaptic neuron and the receptor sites of the postsynaptic neuron. (Of course, the person skilled in the art would understand that other forms of synapses, e.g., axoaxonic synapses and axosomatic synapses, can also be found in the brain.)

The structure of neurons allows for their efficient communication with one another. Neurons can have multiple dendrites and axon terminals, meaning they can synapse and communicate with multiple other neurons (86 billion neurons have trillions of synapses). Further, neurons are arranged in networks with multiple layers. Neuron communication is also dynamic in nature, as the strength of synapses between neurons is constantly changing. The ability of neurons to change and reorganize themselves over time is referred to as 'neuroplasticity'.

Neurons can be referred to by the class of neurotransmitters they produce. Each class of neurotransmitter has unique properties. Some neurotransmitters are inhibitory (inhibits the post-synaptic neurons) and others are excitatory (excites the post-synaptic neurons). One class of neurotransmitter is the 'monoamines'. Monoamines include, e.g., serotonin and noradrenaline.

Early studies of depression identified decreased monoamine function in the brain, leading to the idea that depression symptoms are caused by low levels of monoamines. This has been referred to as the 'monoamine hypothesis' of depression and is the basis for many pharmacological antidepressant treatments, for example, Selective Serotonin Reuptake Inhibitors (SSRIs). Such drugs are intended to correct this imbalance (i.e., increase levels of monoamines, specifically serotonin, in the brain) by inhibiting re-uptake (re-absorption) of the monoaminergic neurotransmitters by pre-synaptic neurons. That is, after the monoamines (serotonin) have been released into the synapse, their re-uptake by the 'upstream' neuron is inhibited by the action of the SSRI. This re-uptake inhibition increases the number of neurotransmitters available for binding to the post-synaptic neuron's receptors [9]. Glutamate (another neurotransmitter) has also been found to be dysregulated in depression; both increases and decreases in glutamate levels have been found in various brain regions in depressed individuals. These imbalances are found in the brain's prefrontal cortex, a key region involved in complex cognitive behavior. Finally, there is also evidence for the dysfunction of GABAergic neurons in depression (neurons related to the effect of gamma-aminobutyric acid (GABA), another neurotransmitter). Reduced GABA concentration in the brain and dysfunction of GABAergic receptors on post-synaptic neurons have both been observed [10].

There are several brain regions involved in regulating emotion, reward, and memory, which together are referred to as the 'limbic system' of the brain. Although there are many brain regions implicated in depression, the limbic system is often a focus of research due to its associations with negative affect, emotion, and other symptoms of depression. Some of the limbic brain regions most commonly implicated in depression include the amygdala, the nucleus accumbens, and the subgenual anterior cingulate cortex (sgACC). The amygdala is a brain region known to be involved in fear and anxiety, while the nucleus accumbens is thought of as the 'reward center' of the brain [9]. The sgACC, a part of the prefrontal cortex, has more recently become known as a key region involved in the symptoms of depression. The sgACC is known to be involved in anticipating and processing emotional events, as well as with sensitivity to threat [11], [12]. Research has shown evidence of over-activation within the sgACC in individuals with depression, and, therefore, this region has become a primary target for treatment [13].

Moreover, although individual brain regions are implicated in the symptoms of depression, there is increasing evidence of dysfunction at a broader level; entire 'networks', or groups of brain regions, need to be considered in depression. Brain imaging research is demonstrating how various brain regions are structurally connected to one another. Recent advancements in brain imaging, such as those in functional magnetic resonance imaging (fMRI), allow observations of correlated or synchronous activity between brain regions when observed over a period of time [14]. Brain networks are commonly defined as follows: they are groups of brain regions that do not necessarily have a direct physical connection, but that exhibit synchronous activity.

Three key brain networks have emerged from the scientific literature that coordinate higher-level cognitive functions such as problem-solving, memory, and emotion. These brain networks are (1) the Executive Control Network (ECN), (2) the Salience Network (SN), and (3) the Default Mode Network (DMN) (see [15], [16]). The ECN is involved in attention and goal-directed tasks, while the SN is involved in processing emotionally salient events. The DMN is a network that is more active when an individual is self-reflecting, remembering events, or imagining the future. The DMN, in particular, has been shown to be overactive in depression and is involved in excessive rumination. In contrast, activity within the ECN, which is typically involved in externally directed activities, has been shown to be diminished in depression [14]. Overall, these networks are involved in a large number of complex functions, and work together to coordinate emotions, thoughts, and behavior. Accumulating evidence suggests that abnormal connectivity both within and between these 'functional' brain networks is related to symptoms of depression.

Pharmacological depression treatments acting on neurotransmitters, such as SSRIs, often show little to no effect in up to 50% of those treated for depression. Recent research has shown that correlated activity within these brain networks may play a critical role in the response to depression treatment. The DMN and ECN are known to be reciprocally connected to the sgACC. Activity within these brain networks influences activity within the sgACC and vice versa. Further, connectivity within these networks has been shown to predict antidepressant treatment response to medications [17].

Further, as is well-known, individual patients usually have individualized responses to such chemical treatments. Many patients rely on complex and expensive "cocktails" of drugs that may or may not work for their specific needs, and these drugs require frequent adjustment before the patient sees any symptom improvement (if they ever do). Additionally, many patients experience harmful side effects from these medications, which are likewise difficult to predict in advance. Similarly, such individualized combinations may interact in detrimental ways with each other and with other medications taken by the patient. Thus, there is clearly a need for less detrimental techniques for relieving neuropsychological symptoms and/or treating and reversing the underlying disorders.

Transcranial magnetic stimulation (TMS) is a well-known and non-invasive technique developed for treating such symptoms and conditions. Conventional TMS and its variations (e.g., repetitive transcranial magnetic stimulation (rTMS), controllable TMS (cTMS), and others) involve passing an electric current through a magnetic coil positioned near a patient's head. The electric current creates a magnetic field around the coil, which induces a corresponding electrical field in the patient's brain. (These relationships between current, magnetic field, and electrical field are well-known electromagnetic effects). The electrical field in the patient's brain affects the transmembrane current in neurons, resulting in depolarization (making the neuron less negatively charged and, thus, excited) or in hyperpolarization (making the neuron more negatively charged and, thus, inhibited). That is, targeted TMS can be used to excite or inhibit neurons in a specific region of the brain, which can increase or decrease synaptic connectivity in that region.

However, these conventional versions of TMS also have drawbacks. In order for the electric field induced within the brain to be large enough to have an appreciable excitatory effect, TMS devices must operate at high voltages (up to around 2,000 V) to generate a high current (over 10,000 A). Safely regulating such high voltages requires specific technology and devices. In particular, few practically available switches are able to regulate these voltages.

As a result, all TMS devices currently approved by the US Food and Drug Administration use the same type of switch, a semiconductor switch known as a Silicon Controlled Rectifier (SCR) or "thyristor". This particular switch has unique ON/OFF oscillatory dynamics. When this switch between the voltage bank and the coil is triggered ON, it delivers the first half of the current pulse (i.e., the positive current flow from the energy source/voltage bank into the coil). Then, because of its internal structure, this switch automatically returns to the OFF position. When the switch has returned to OFF (i.e., energy is no longer being delivered into the coil from the voltage bank/energy source), the energy contained in the coil must be dissipated through heat and/or recovered back into the bank. This recovery corresponds to the second half of the pulse (the negative current flow out of the coil back to the voltage bank/energy source). Conventional devices thus generate a full sine wave current pulse, resulting in the induction of a corresponding cosinusoidal electrical field in the brain.

Because of high current flows, a significant amount of energy generally remains in the coil of conventional devices when an SCR switch returns to OFF. This amount of energy is typically on the order of several hundred joules. Dissipating that much energy through heat dissipation alone is unsafe: the coil (which is positioned very close to a patient's head) could become extremely hot. Therefore, for conventional devices, the energy must be recovered back into the voltage bank/energy source through a separate circuit.

However, some of the energy is still dissipated as heat (i.e., not all of the energy is recovered). This is known as "roll-off". Because of the size of the voltage bank used, conventional devices using thyristor switches tend to have a fairly high roll-off loss (as shown in FIG. 1A). Roll-off is also most significant at higher voltages/higher device intensities and within the first few pulses.

However, as will be discussed further below, bidirectional pulses can be less effective in relieving symptoms than unidirectional pulses. That is, the person skilled in the art would understand that the second half of a bidirectional pulse (i.e., the result of the negative current from the coil returning to the energy source) could reduce or, in some instances, effectively cancel out the benefits of the first half of the pulse (i.e., the result of the positive current to the coil from the energy source). Although some devices using thyristors can generate monophasic pulses, these devices are limited to low frequency pulse repetition and single pulses, and are not well-suited for therapeutic applications.

Accordingly, there is a need for methods of generating unidirectional monophasic (or, at least, near-unidirectional monophasic) pulses repeated with high frequencies (suitable for therapeutic purposes) while minimizing roll-off problems.

SUMMARY

This document discloses a method of generating a monophasic pulse using a device having a voltage bank with an adjustable voltage level, and a use of such a pulse to induce a current flow in an individual's brain. The voltage level is controlled by a voltage control device. In some embodiments, the voltage control device comprises one or more switches, such as IGBTs, and/or one or more inductors. Energy from the voltage bank is discharged into a magnetic coil of the stimulation device (positive, increasing current). When the energy in the coil reaches a predetermined peak level, the voltage of the voltage bank is rapidly changed from a first level to a second level, such that the majority of the energy in the coil is recovered (positive, decreasing current) while the voltage level is at the second level.

In some embodiments, the voltage levels are selected so that energy recovery (i.e., "fall time") takes longer than the time required to reach said predetermined peak value (i.e., "rise time"), thereby creating a unidirectional monophasic triangular pulse. In such embodiments, the first level is at least 5 times the second level. In other embodiments, the unidirectional monophasic triangular pulse is created by selecting the voltage levels so that the rise time is longer than the fall time. In such embodiments, the second level is at least 5 times the first level.

In a first aspect, this document discloses a method for generating a pulse using a device comprising a circuit, wherein said circuit comprises:

an energy source for delivering energy to said circuit and for recovering at least a portion of said energy from said circuit, said energy source having an adjustable voltage level;

at least one voltage control device for controlling said voltage level;

a coil through which said energy is passed, such that passage of said energy creates a magnetic field around said coil, and wherein said coil is positioned near an individual's brain such that said magnetic field thereby induces a current flow in said individual's brain, and said method comprises the steps of:

delivering said energy to said circuit while said voltage level of said energy source is at a first level; and when said energy in said coil reaches a predetermined peak value, changing said voltage level to a second level, such that a majority of said energy is recovered while said voltage level is at said second level, wherein:

said first level is at least 5 times said second level; or said second level is at least 5 times said first level, and wherein said pulse is unidirectional, monophasic, and triangular.

In a further embodiment, this document discloses a method wherein said at least one voltage control device comprises at least one semiconductor switching device.

In a further embodiment, this document discloses a method wherein said at least one semiconductor switching device is an insulated gate bipolar transistor (IGBT).

In a further embodiment, this document discloses a method wherein said at least one voltage control device further comprises at least one inductor.

In a further embodiment, this document discloses a method wherein said method is used to treat a neurological condition or a neurophysiological condition of said individual.

In a further embodiment, this document discloses a method wherein said energy source is an energy storage device for storing energy received from a power source.

In a further embodiment, this document discloses a method wherein said energy storage device is a capacitor.

In a further embodiment, this document discloses a method wherein said energy storage device is a capacitor bank.

In a second aspect, this document discloses a use of an electrical pulse to induce a current flow in an individual's brain, wherein said electrical pulse is a unidirectional monophasic and triangular pulse.

In a further embodiment, this document discloses a use wherein said pulse is generated by a device having an adjustable voltage level, wherein said pulse ha a rise time and a fall time, wherein said rise time is a first time during which an amplitude of said pulse is increasing and wherein, during said rise time, said voltage level is a first level, and wherein said fall time is a second time during which said amplitude of said pulse is decreasing, and wherein, during said fall time, said voltage level is a second level.

In a further embodiment, this document discloses a use wherein said first level is at least 5 times said second level.

In a further embodiment, this document discloses a use wherein said second level is at least 5 times said first level.

In a further embodiment, this document discloses a use wherein said pulse is used to treat a neurological condition or a neurophysiological condition of said individual.

BRIEF DESCRIPTION OF THE DRAWINGS

The present invention will now be described by reference to the following figures, in which identical reference numerals refer to identical elements and in which.

DETAILED DESCRIPTION

The present invention generates a unidirectional monophasic triangular pulse in a stimulation device that is placed near an individual's (patient's) head (and thus near their brain). The unidirectional monophasic triangular pulse generates a unidirectional current flow within the individual's brain. Such a pulse can be used in treating neurological and/or neuropsychological conditions and disorders of the individual and can also mitigate or relieve symptoms of such conditions, including physical, neurological, and psychological symptoms.

Figure 1A:
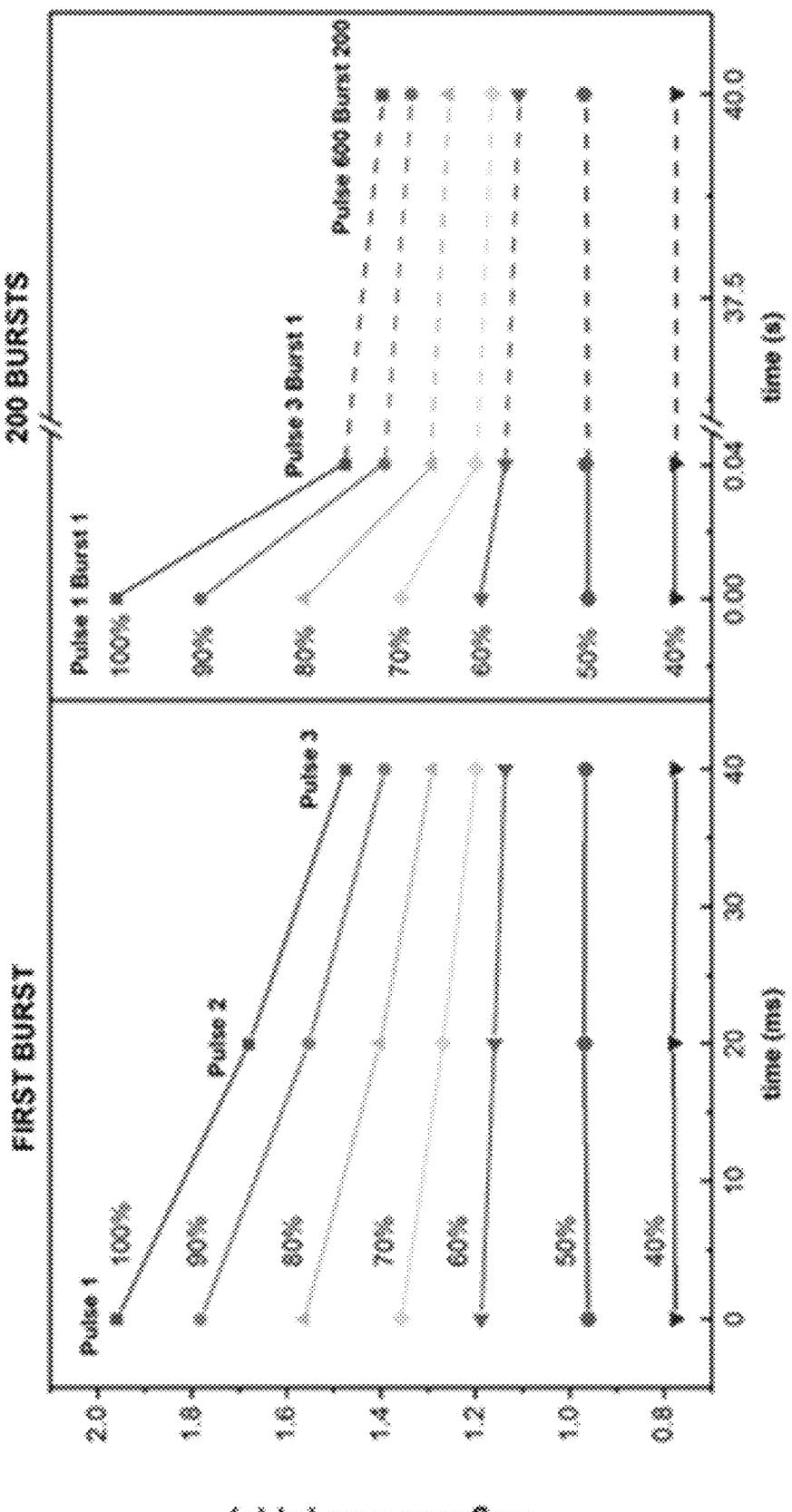
FIG. 1A shows roll-off in conventional TMS devices, according to the prior art.
Figure 1B:
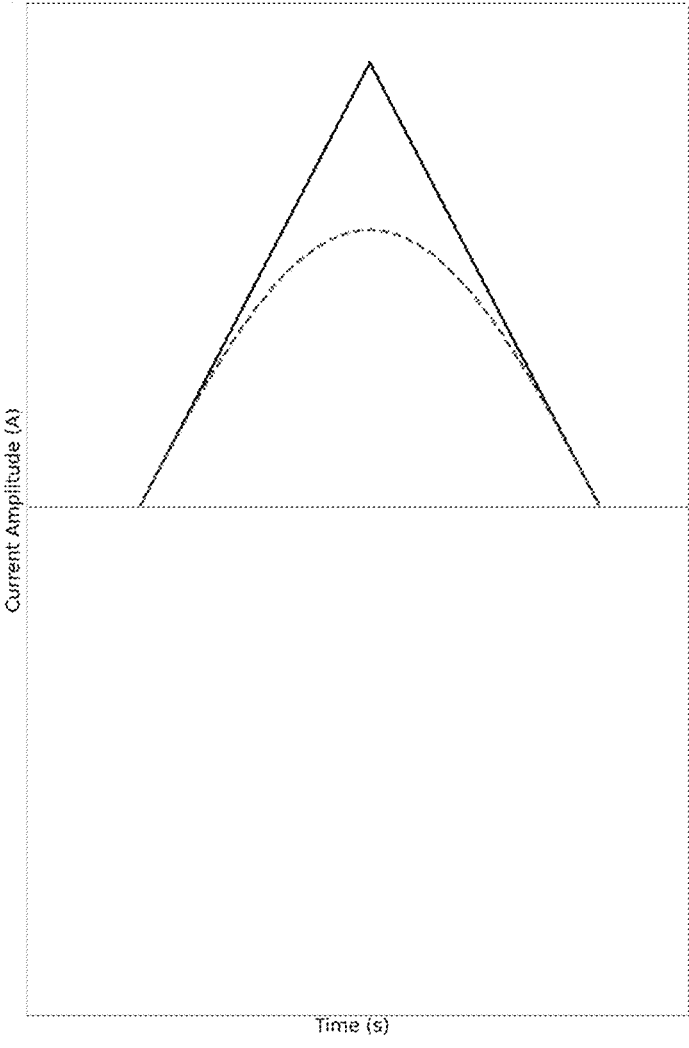
FIG. 1B is a plot of a monophasic pulse, as theoretically known in the prior art.

As is well-known in the art, a pulse may be described according to several characteristics. In particular, useful characterizations of pulses include the directionality, the phase, and the shape of each pulse. Herein, the directionality of a pulse is characterized as either "unidirectional" or "bidirectional". A unidirectional pulse used in a treatment device is a pulse that induces a current flow in only one direction in the brain, while a bidirectional pulse in a treatment device induces a current in the brain to flow in a first direction and then to reverse into the other or reverse direction. Monophasic and biphasic pulses can be described as follows: a biphasic pulse has two peaks, one with a positive amplitude (i.e., an amplitude on the positive side of the x-axis) and one with a negative amplitude (i.e., an amplitude on the negative side of the x-axis). A monophasic pulse, however, only has a single positive peak and, if plotted, does not cross the zero-amplitude axis (or the x-axis in a conventional plot). Pulse shape refers to the shape of the pulse when plotted against time: that is, a "triangular" pulse creates a triangle shape on the plot, while a sinusoidal pulse follows a sinusoidal path and has a sinusoidal shape. A unidirectional monophasic triangular pulse (shown for reference in FIG. 1B) would thus be understood to be a pulse having a single positive peak that, when plotted on a current vs. time plot, makes a triangular shape in the first quadrant (i.e., positive current, positive time). (Of course, the person skilled in the art would understand that, in practice, there may be a small-amplitude portion of the pulse below the horizontal axis (i.e., with negative current); however, such portion would be much smaller than the rest of the pulse.) Such a pulse induces a current flow in only one direction in a patient's brain.

The stimulation device used to deliver such a pulse comprises an energy source/bank, a voltage control device, and a magnetic coil. The voltage bank has an adjustable voltage level, and the voltage control device is configured to rapidly change the voltage level once the energy in the coil has reached a predetermined peak intensity. This rapid change means that the majority of the energy remaining in the coil is returned to the energy source, rather than dissipating as heat while the coil is at its peak value.

The voltage levels can be individualized for each patient. In particular, in embodiments where the first level is higher than the second level, the first level is preferably individualized for each patient to be higher than that patient's individual motor threshold (MT, a well-known metric representing the voltage required to induce movement in the patient). The second level in such embodiments must be smaller than the individualized motor threshold (i.e., the second level should not induce movement). A second voltage level close to zero is preferable. However, in some embodiments, the second voltage level can trigger neural effects (i.e., be higher than near-zero but still below the motor threshold). Of course, in embodiments where the second level is selected to be higher than the first level, the above amplitudes would be reversed (the second level being above the patient's MT and the first level being lower/close to zero).

The peak value that triggers the change in voltage level is dependent on various factors, as would be understood by the person skilled in the art. These factors include the inductance L of the magnetic coil and the voltage used V, as follows:

$$V = L\frac{di}{dt}$$

where $$\frac{di}{dt}$$

is the change in current i in the coil over time t. In a typical but non-limiting example, the peak current (defined as $i_{peak}$=di–0) is thus 14,000 A when a voltage of 2,000V is delivered over 100 μs, given a coil inductance of approximately 14 μH.

As should be clear, the device is preferably capable of delivering more than one type of pulse, depending on a desired implementation/application. Similarly, the device is preferably operable at a range of voltages and frequencies, and preferably is able to generate magnetic fields of various strengths. In some implementations, the device is used to deliver voltages of up to 2,000 V. For these implementations, the device may be useful for delivering up to 2,000 V at a frequency of up to 20 Hz. Preferably, the device is also useful for providing stimulation at a frequency of 10 Hz, and for providing intermittent theta burst stimulation (iTBS, i.e., 3 pulses in a 50 Hz burst repeated at 5 Hz). Note, however, that at all frequencies, there is a limit to the number of pulses that can be delivered without a break in a train to avoid seizures in the patient. At 10 Hz, the break is required at 4 sec (40 pulses). In iTBS, the break is required at 2 sec (30 pulses). For frequencies greater than 20 Hz, the break is required at 1 sec (20 pulses). The US Food and Drug Administration (FDA) has approved stimulation at 10 Hz and iTBS, both of which are typical stimulation techniques. Most conventional commercial rTMS units have voltages between 1500 V to 2000 V with the coil inductances ranging between 10 μH to 15 μH. As would be clear to the person of skill in the art, the triangular pulse generated by the methods of the present invention may require specific hardware components, specific software components and/or modules passing instructions to those hardware components, or both.

Figure 2:
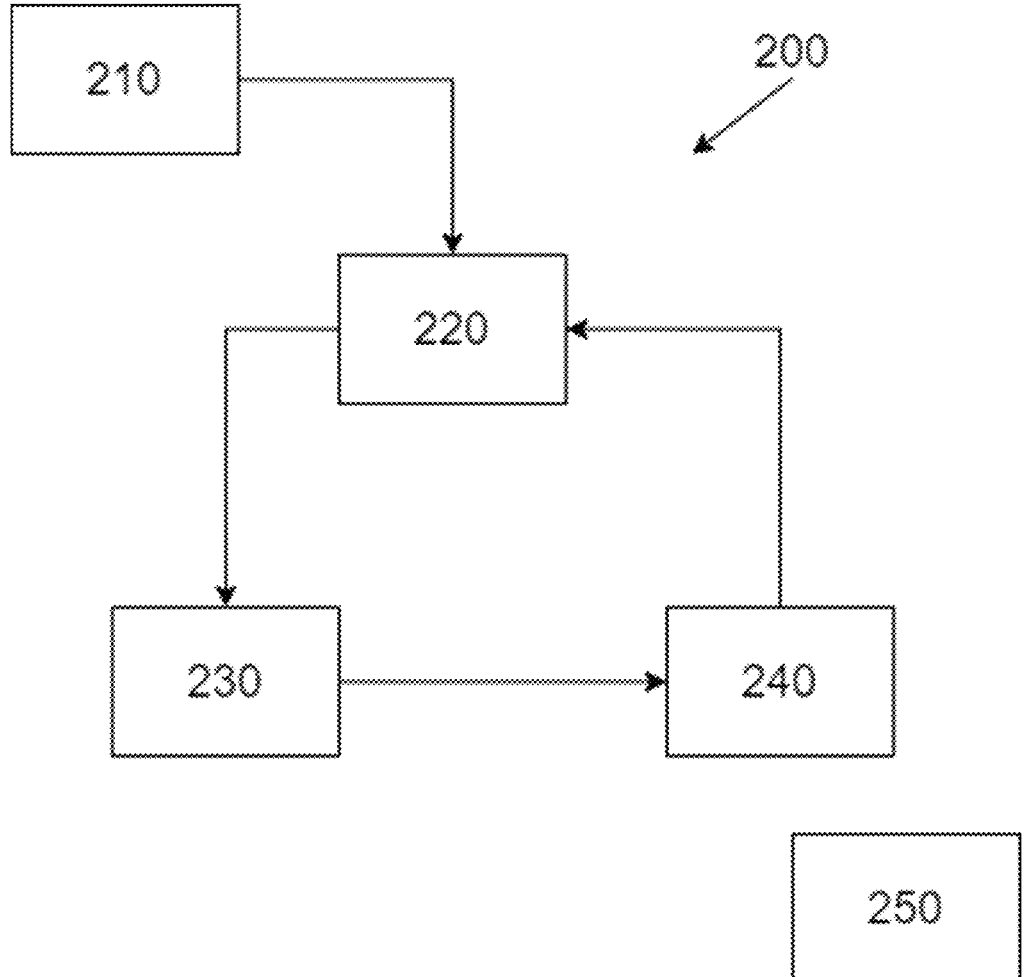
FIG. 2 is a block diagram showing a system that may be used to implement a method according to one aspect of the invention.

FIG. 2 is a block diagram of a system 200 using such a device. The system 200 has a power source 210 that is connected to an energy source 220 ("voltage bank"). The voltage in the system is controlled by a voltage control device 230. Energy is passed to the magnetic coil 240, creating a magnetic field that induces a current flow in the user's brain 250. Energy is then recovered by the voltage bank 220 when the voltage bank is at a second voltage level, which may be higher or lower than the delivery voltage.

Various circuit designs can be used for such an application. In particular, circuits in which the voltage control device comprises at least one insulated gate bipolar transistor (IGBT), rather than a thyristor, may be used. Recall that, where a conventional thyristor is used, energy recovery begins once the switch has automatically returned to OFF. In contrast, the dynamics of IGBT switches mean that the switch can be turned off at the peak level, allowing energy recovery to begin. Further, circuits such as that disclosed in [18] below may be used. Suitable designs may include one or more inductors, switches, and/or other components. The energy source may be an energy storage device, such as a capacitor or capacitor bank. The power source can be an external power source or an internal power source, depending on the implementation of the device. In some embodiments, the power source is a general-purpose utility power supply (i.e., mains or wall power).

However, as should be clear, nothing in the present application is intended to limit the methods and uses presented herein to any specific design. Rather, any device designed such that the voltage bank has an adjustable voltage level that responds to a voltage control device should be understood to be suitable for use with the present invention. Additionally, as should be understood, in some embodiments, the voltage bank and voltage control device may be integrated together as a single unit.

Note that, in addition to having an adjustable voltage level, the voltage bank is preferably much larger than conventional voltage banks of conventional TMS devices. Larger banks can be used to compensate for heat dissipation and thus prevent or mitigate roll-off, allowing multiple pulses in a pulse train to be delivered without a significant decrease. Preferably, the subsequent pulses are within ±5% of the intensity of the first pulse. The voltage bank is preferably at least 10% larger than conventional banks.

Figure 3A:
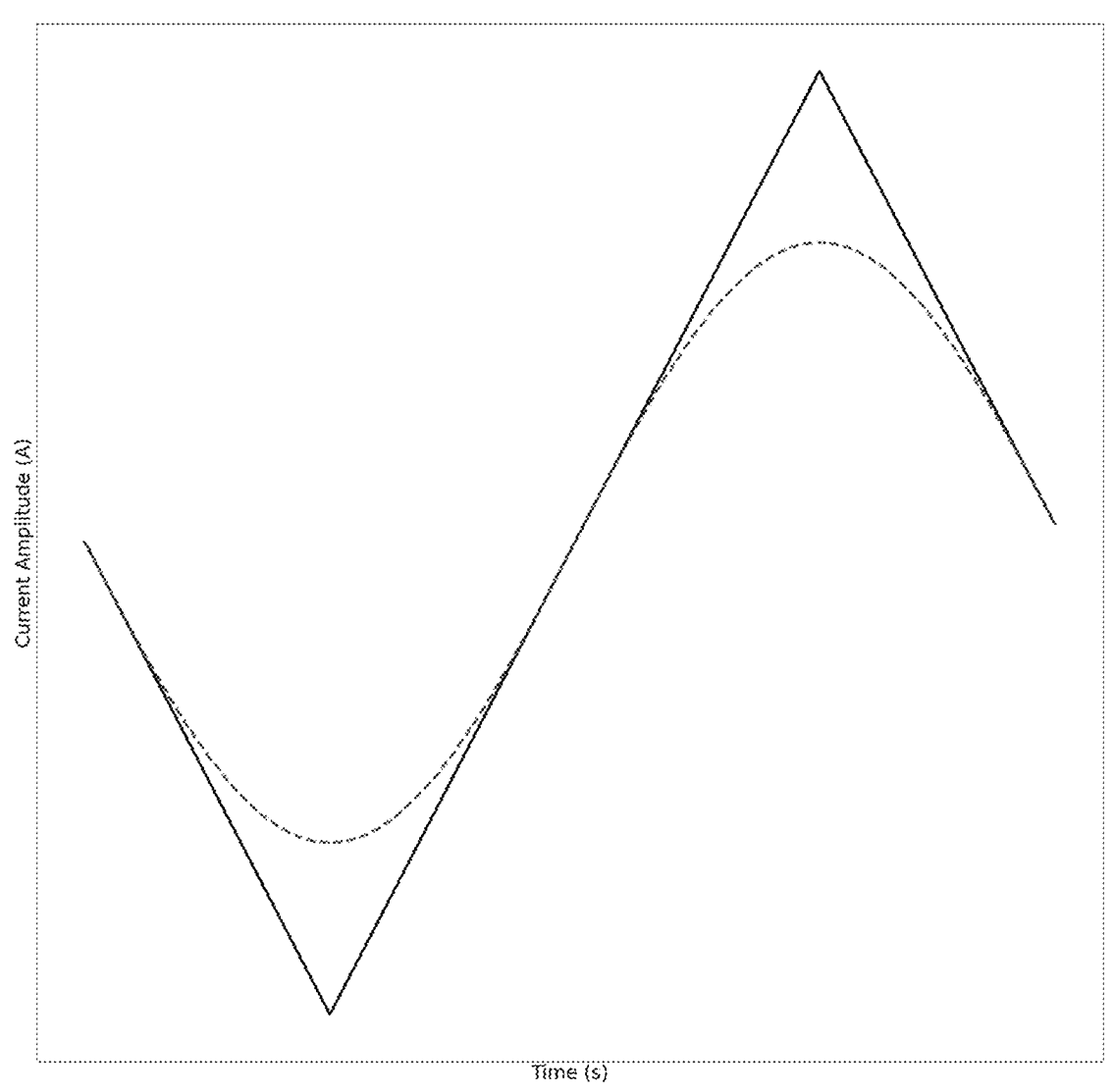
FIG. 3A is a plot of a biphasic sinusoidal pulse produced by conventional TMS devices (dashed line), and of a bidirectional biphasic triangular pulse (solid line) produced according to the present invention.
Figure 3B:
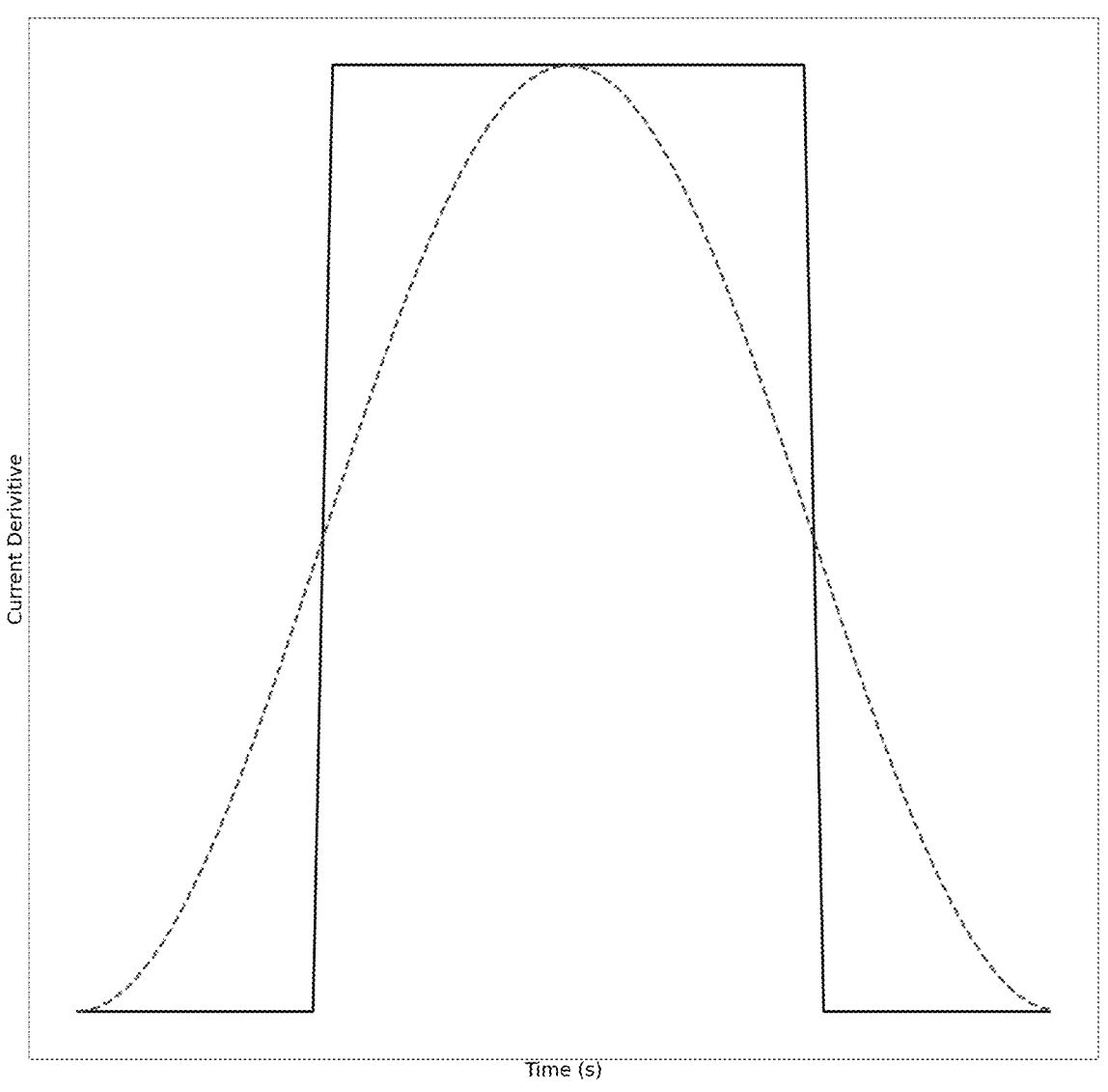
FIG. 3B is a plot of the electrical fields induced within an individual's brain by the corresponding pulses of FIG. 3A.

Referring now to FIG. 3A, a conventional TMS pulse shape is shown (the dashed line). (The solid line, as will be discussed further below, is a triangular pulse.) FIG. 3B shows the induced electric field within the brain, corresponding to the electrical pulse—that is, the dashed line in FIG. 3B is a plot of the electric field induced by the dashed sinusoidal pulse of FIG. 3A. As would be understood, the field induced within the brain goes with the first derivative of the pulse in the device. That is, the pulse in FIG. 3A is a sinusoidal curve, and the corresponding field in FIG. 3B is the derivative of that sinusoidal curve (i.e., is co-sinusoidal). As described above, a positive sinusoidal pulse followed by its inverse is not always effective at symptom reduction: that is, the electrical effect induced in one direction could be counteracted by the second half of the pulse. Triangular-shaped pulses, such as that shown as a solid line in FIG. 3A, are preferable, as (when correctly calibrated) the induced field simply follows a rectangular "pulse-on/pulse-off" shape (the corresponding solid line in FIG. 3B).

Figure 4A:
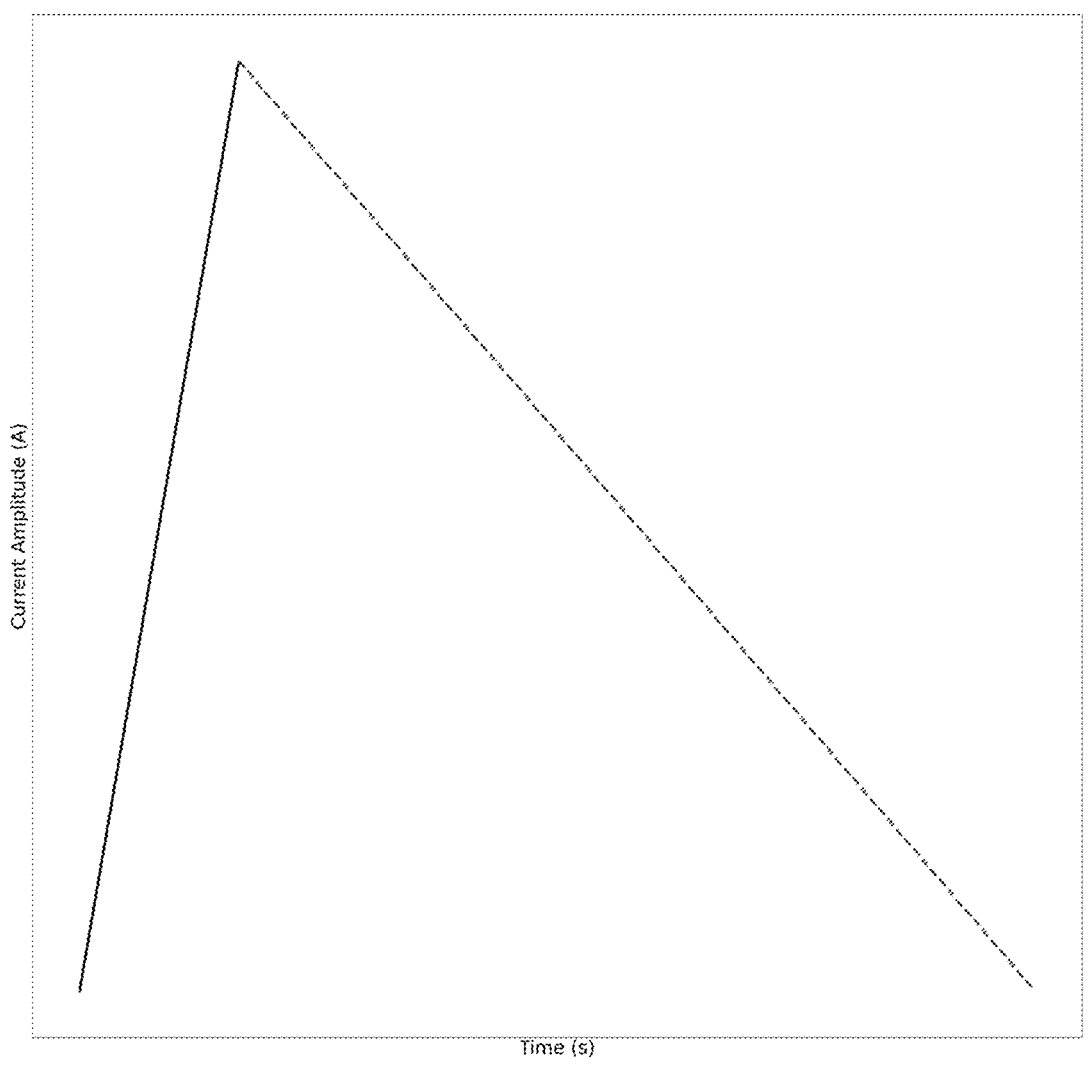
FIG. 4A is a plot of a unidirectional monophasic triangular pulse produced according to the present invention.

However, FIG. 4A shows an even more preferable device pulse shape: that is, a rapid positive rise followed by a slow fall. This is a triangular current pulse. As should be clear, a plot of the corresponding voltage against time would appear essentially rectangular: i.e., a first constant level followed by a lower constant level.

Figure 4B:
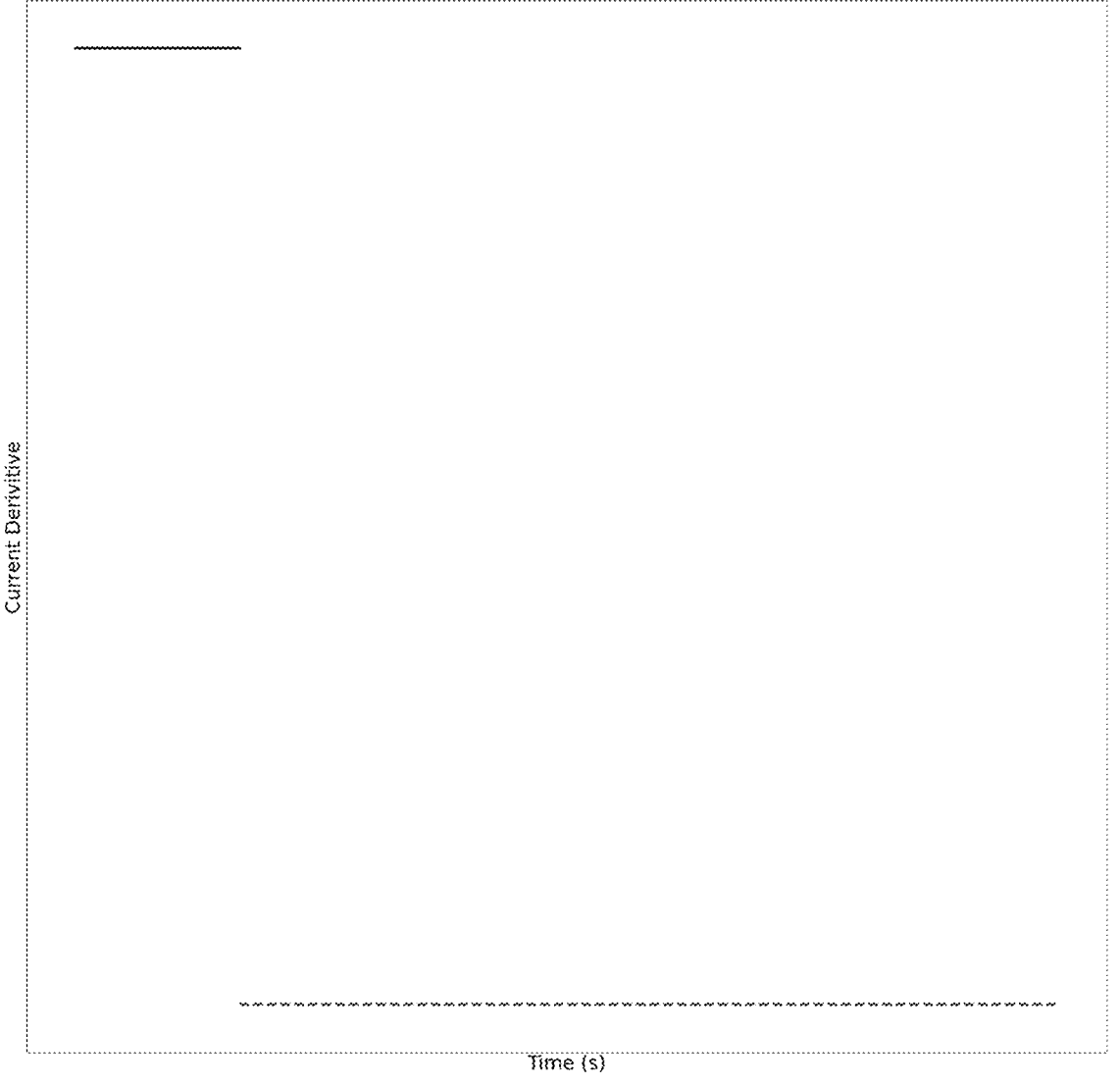
FIG. 4B is a plot of the electrical fields induced within an individual's brain by the corresponding pulse of FIG. 4A.

FIG. 4B shows the electrical field induced within the brain by the current pulse of FIG. 4A. As can be seen, the plot of this field against time is also essentially rectangular. There is a positive portion that occurs in a short time period followed by a longer-lasting steady-state period having negligible effects (i.e., a short burst followed by a longer 'OFF' period), rather than counteracting positive and negative sinusoidal pulses. This short burst (i.e., a burst with a very short time duration) and long OFF period (i.e., a longer time duration when the power drops off) constitute what is, essentially, a monophasic (unidirectional) pulse (or, at least, a very near monophasic pulse). The majority of the energy stored in the coil is recovered by the energy source during this OFF period.

As would be understood by the person skilled in the art, because of the time required for energy buildup, an ideal unidirectional pulse may not be feasible with all TMS devices. However, the faster the voltage level can be changed to the second level, the closer the pulse will be to unidirectional. In some implementations, the voltage drop can occur on the order of hundreds of nanoseconds (i.e., within approximately 1 microsecond), depending on intensity, temperature and coil inductance.

To obtain the unidirectional monophasic triangular pulse shape of FIGS. 4A and 4B, the voltage levels are selected so that the first level (the higher level) is at least 5 times the second level (the lower level). That is, if the first level is x and the second level is y, then $x \geq 5y$. When such voltages are selected, the fall time of the device pulse will be approximately 5 times longer than the rise time. (Preferably, the fall time is at least 5 times longer than the rise time, but heat loss from the coil may affect that recovery.) Accordingly, the ratio between the time required for the coil to reach its predetermined peak value (rise time) and the time taken to recover the energy from the coil (fall time) is approximately 1:5. This means that, if the time required for the coil to reach a peak value from a starting value is x time units, then the time required for the coil to drop from this peak value back to the starting value is 5x. Voltage levels that result in longer fall times are even more preferable. The person skilled in the art would understand that the possible length of the rise time and fall time (and the possible ratios between them) would depend on the frequency of the pulse used. As a non-limiting example, assuming a 20 Hz repetition, the duration of the entire pulse cannot exceed 50 milliseconds. In such an implementation, assuming a rise time of 150 µs and allowing a small amount of time at peak, the fall time would be less than 49.8 ms. In this example, the rise time:fall time ratio would be 1:332.

Additionally, with regard to determining the preferable rise time:fall time ratio and the voltage levels required to obtain that ratio, the width of the pulse at the first level—that is, the duration of the positive portion of the pulse in FIG. 4B—may be noted as a factor. That is, although larger ratios are often preferable, there may be a point at which the benefit of the larger ratio is undercut by the drawbacks of having only a very short pulse. That is, if the positive portion of the pulse (corresponding to the rise time) is very short (<60 µs), desired excitation or inhibition of specific neurons might not occur.

It should be noted that the above voltage level relationships result in a unidirectional monophasic pulse of which the rise time is shorter than the fall time. In other embodiments, however, a unidirectional monophasic pulse can be created with the rise time being longer than the fall time. That is, using the variables above for the first voltage level x and the second voltage level y, a unidirectional monophasic pulse is created when $y \geq 5x$ (i.e., when the second level is at least 5 times the first level). When $y = 5x$, the pulse would have a rise time:fall time ratio approximately equal to 5:1. The person skilled in the art would understand that any suitable rise time:fall time ratios may be obtained by selecting corresponding voltage levels.

Test Results—Safety Study

Several tests of a TMS device having a voltage bank with a rapidly adjustable voltage level were performed in a safety study. The voltage levels of the device used in the study could be set to so that the rise and fall times of triangular-shaped pulses were equal (i.e., a bidirectional biphasic pulse) or so that the fall time was longer than the rise time (i.e., the unidirectional monophasic pulse of the present invention). The device used in the study was a proprietary investigational device, which comprises a cooled, figure-8-shaped magnetic coil applicator, applied to the participants' heads above the left dorsolateral prefrontal cortex (DLPFC). However, of course, any device capable of producing a suitable monophasic pulse and suitable for desired applications (e.g., safe for therapeutic use) could be used to deliver the pulse.

The study participants comprised both healthy volunteers and patients with "treatment-resistant depression" (TRD, categorized as a condition where a patient taking at least one conventional pharmaceutical anti-depressant at its maximum recommended dose is still not in remission with respect to their depression symptoms—that is, is still not symptom-free). This study randomized between a bidirectional biphasic triangular pulse and a unidirectional monophasic triangular pulse. The TMS parameters and treatment settings used are listed in Table 1.

Note that, to clearly compare the effects of the two kinds of triangular pulse, the pulse width of the unidirectional monophasic triangular pulse was set to double that of the bidirectional biphasic triangular pulse: as discussed above, the second half of the unidirectional pulse has negligible effects, while the entire bidirectional biphasic pulse has an effect on the patient's brain.

TABLE 1

| | Healthy volunteers | | TRD patients | |
| | Bidirectional biphasic triangular pulse | Unidirectional monophasic triangular pulse | Bidirectional biphasic triangular pulse | Unidirectional monophasic triangular pulse |
| --- | --- | --- | --- | --- |
| Pulse rise time (μs) | 60 | 60 | 60 | 60 |
| Effective pulse width (μs) | 120 | 60 | 120 | 60 |
| Repetitive rate (Hz) | 20 | 20 | 20 | 20 |
| Train duration (sec) | 1 | 1 | 1 | 1 |
| Intertrain interval (sec) | 5 | 5 | 5 | 5 |
| % Motor Threshold | 120 | 120 | 120 | 120 |
| Number of trains | 150 | 150 | 150 | 150 |
| Pulse per sessions | 3,000 | 3,000 | 3,000 | 3,000 |
| Treatment duration (min) | 15 | 15 | 15 | 15 |
| Session per week | 3 | 3 | 5 | 5 |
| Full treatment (week) | 1 | 1 | 6 | 6 |
| Total number of pulses | 9,000 | 9,000 | 90,000 | 90,000 |

Adverse events experienced by any of the ten healthy participants during the study sessions are shown in Table 2 below for each type of adverse event reported. They are shown as "Severity (# of participants reporting)". These adverse events were generally mild and not long-lasting, and are similar to the results of conventional TMS.

TABLE 2

| Adverse Event | Stimulation Type | Session 1 | Session 2 | Session 3 |
| --- | --- | --- | --- | --- |
| Light | Unidirectional | Mild (2) | — | — |
| Headedness | Bidirectional | Mild (2) | — | Mild (1) |

TABLE 2-continued

| Adverse Event | Stimulation Type | Session 1 | Session 2 | Session 3 |
| --- | --- | --- | --- | --- |
| Headache | Unidirectional | Mild (1) | Mild (1) | Mild (1), Moderate (1) |
| | Bidirectional | — | — | — |
| Drowsy | Unidirectional | — | Mild (1) | — |
| | Bidirectional | Mild (1) | Mild (1) | Mild (1) |
| Dizziness | Unidirectional | — | — | Mild (1) |
| | Bidirectional | Mild (2) | Mild (1) | — |
| Disorientation | Unidirectional | — | Mild (1) | — |
| | Bidirectional | — | — | — |
| Dry mouth | Unidirectional | Mild (1) | — | — |
| | Bidirectional | — | — | — |
| "High feeling" | Unidirectional | — | — | — |
| | Bidirectional | — | Mild (1) | — |

Figure 5:
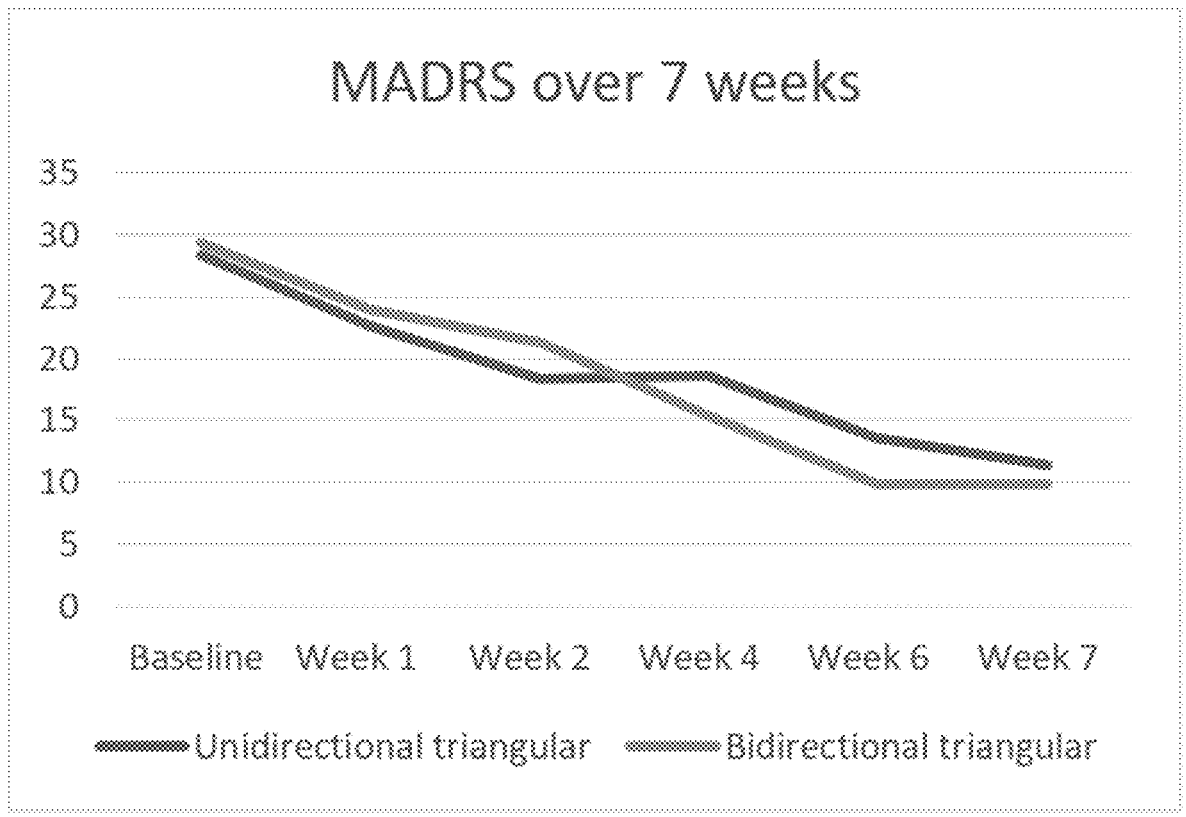
FIG. 5 shows average scores on the Montgomery-Asberg Depression Rating Scale (MADRS) for participants in a safety study of the present invention.

The well-known Montgomery-Asberg Depression Rating Scale (MADRS) was then used to evaluate the efficacy of the bidirectional biphasic pulse and the unidirectional monophasic pulse of the present invention over the full treatment period for the eighteen (18) TRD patients in the safety study. FIG. 5 shows the visible reduction of the average MADRS score of the TRD participants over the course of the safety study. (Note that a higher MADRS score indicates more severe depression than a lower score does). As can be seen, over the course of the study, the nine (9) participants receiving the unidirectional monophasic-pulse treatment showed good results, decreasing from an original baseline average score of 28 to a score value of 12. The nine (9) participants receiving the bidirectional biphasic-pulse treatment also showed good results, decreasing from an original baseline average score of 29 to a score value of 10.

Table 3, below, shows the response and remission rates of the TRD patients against various historical data from conventional TMS treatments that use bidirectional biphasic sinusoidal pulses ([19] and [20]), as well as against a large-scale study of the efficacy of pharmaceutical treatments ([21]) and against historical averages for the effectiveness of electro-convulsive therapy (ECT, transcranial current stimulation that triggers seizures). A patient is considered to "respond" to the treatment if their MADRS score at the end of the treatment was 50% or lower than their MADRS score at the beginning of the treatment. A patient is considered to be in remission if their MADRS score at the end of the treatment was a value of 7 or less. (Note that ECT generally predates the MADRS test and thus the response and remission values for ECT are comparatively subjective.)

TABLE 3

| | Participants | Response rate | Remission rate |
| --- | --- | --- | --- |
| Unidirectional triangular | 9 | 77% | 55% |
| Bidirectional triangular | 9 | 77% | 55% |
| Combined | 18 | 61% | 39% |
| O'Reardon et. al., 2007 [19] | 165 | 24% | 14% |
| Meta-analysis 2016 [20] | >200 | 25% | 17% |
| STAR*D level 3 [21] | >4000 | 20% | 14% |
| ECT | Historical average | 80% | 70% |

As can be seen, the unidirectional monophasic triangular pulse was most effective, but even the bidirectional biphasic triangular pulse showed better results than almost all conventional treatments (with the exception of electro-convulsive therapy, for which only historical averages are available). As such, the unidirectional monophasic triangular pulse of the present invention appears highly effective.

Additionally, the adverse events experienced by the TRD patients in the study were comparable to those experienced by patients treated with conventional biphasic sinusoidal TMS devices and methods at frequencies of 10 Hz and 50 Hz theta burst. Adverse events can be categorized as follows:

Physical: light-headedness, headache, drowsiness, nausea, jaw/muscle pain, heart palpitations, chest pain, difficulty breathing, dry mouth, blurred vision;

Psychological: agitation, irritation, fatigue, depression, anxiety, mood swings, difficulty concentrating, hallucinations; and Psychomotor: seizure, tremors, dizziness, spinning sensation, lack of coordination, disorientation, weakness/lack of energy.

Table 4 below shows the number of TRD patients in the safety study who experienced acute adverse events (immediately after treatment session) by week and stimulation type:

TABLE 4

| Week | Physical Unidirectional (N; %) | Physical Bidirectional (N; %) | Psychological Unidirectional (N; %) | Psychological Bidirectional (N; %) | Psychomotor Unidirectional (N; %) | Psychomotor Bidirectional (N; %) |
|---|---|---|---|---|---|---|
| 1 | 6 (66.7) | 7 (63.6) | 4 (44.4) | 4 (36.4) | 2 (22.2) | 4 (36.4) |
| 2 | 4 (44.4) | 3 (30) | 5 (55.6) | 3 (30) | 2 (22.2) | 3 (30) |
| 3 | 3 (33.3) | 3 (30) | 3 (33.3) | 0 | 2 (22.2) | 1 (10) |
| 4 | 3 (33.3) | 2 (20) | 2 (22.2) | 3 (30) | 1 (11.1) | 1 (10) |
| 5 | 3 (33.3) | 2 (22.2) | 3 (33.3) | 1 (11.1) | 0 | 1 (11.1) |
| 6 | 3 (33.3) | 2 (22.2) | 1 (11.1) | 0 | 0 | 1 (11.1) |

Table 5 shows the number of patients who experienced short-term adverse events (within 24 hours of the treatment session) by week and stimulation type:

| Week | Physical Unidirectional (N; %) | Physical Bidirectional (N; %) | Psychological Unidirectional (N; %) | Psychological Bidirectional (N; %) | Psychomotor Unidirectional (N; %) | Psychomotor Bidirectional (N; %) |
|---|---|---|---|---|---|---|
| 1 | 7 (87.5) | 7 (70) | 6 (75) | 8 (80) | 5 (62.5) | 4 (40) |
| 2 | 3 (37.5) | 4 (44.4) | 5 (62.5) | 5 (55.6) | 3 (37.5) | 4 (44.4) |
| 3 | 5 (62.5) | 3 (33.3) | 5 (62.5) | 4 (44.4) | 2 (25) | 2 (22.2) |
| 4 | 3 (37.5) | 3 (33.3) | 5 (62.5) | 4 (44.4) | 1 (12.5) | 1 (11.1) |
| 5 | 2 (25) | 2 (25) | 4 (50) | 2 (25) | 1 (12.5) | 2 (25) |
| 6 | 4 (50) | 2 (25) | 4 (50) | 2 (25) | 1 (12.5) | 2 (25) |

As can be seen, the adverse events were most common near the beginning of the treatments.

Figure 6:
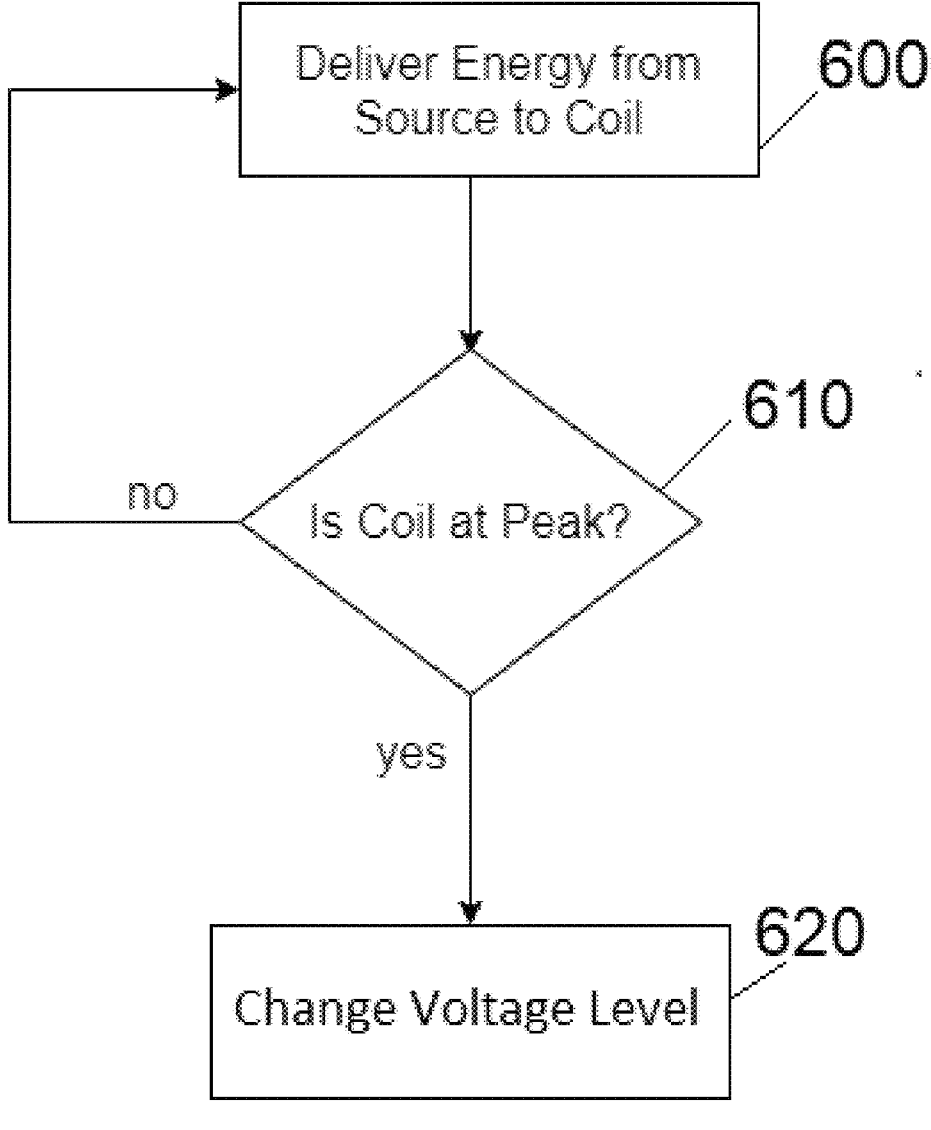
FIG. 6 is a flowchart detailing a method according to one aspect of the present invention.

Referring now to FIG. 6, a flowchart detailing a method according to one aspect of the invention is shown. At step 600, energy is delivered to a coil of a stimulation device from the energy source (i.e., the voltage bank). When the coil has reached a predetermined peak value (i.e., a peak intensity, assessed at step 610), the voltage level is rapidly changed, as described above, using the voltage control device of the stimulation device (step 620). To obtain a unidirectional monophasic pulse, the voltage levels are selected such that the first level is at least 5 times the second level, or such that the second level is at least 5 times the first level.

As noted above, for a better understanding of the present invention, the following references may be consulted. Each of these references is hereby incorporated by reference in its entirety:

[1] World Health Organization. Fact Sheet: Depression. 30 Jan. 2020. https://www.who.int/news-room/fact-sheets/detail/depression.

[2] Lim, G. Y., Tam, W. W., Lu, Y., Ho, C. S., Zhang, M. W., & Ho, R. C. (2018). Prevalence of Depression in the Community from 30 Countries between 1994 and 2014. *Scientific Reports,* 8(1), 1-10. DOI: https://doi.org/10.1038/s41598-018-21243-x.

[3] Nestler, E. J., Barrot, M., Dileone, R. J., Eisch, A. J., Gold, S. J., & Monteggia, L. M. (2002). Review: Neurobiology of Depression: The Focus of Efforts to Understand the Pathophysiology. *Neuron,* 34.

[4] Krishnan, V., & Nestler, E. J. (2008). The Molecular Neurobiology of Depression. *Nature,* 455 (7215), 894-902. https://doi.org/10.1038/nature07455

[5] Saveanu, R. V., & Nemeroff, C. B. (2012). Etiology of Depression: Genetic and Environmental Factors. *Psychiatric Clinics of North America,* 35(1), 51-71. https://doi.org/10.1016/j.psc.2011.12.001

[6] McMahon, F. J. (2018). Population-based Estimates of Heritability Shed New Light on Clinical Features of Major Depression. *American Journal of Psychiatry,* 175(11), 1058-1060. https://doi.org/10.1176/appi.ajp.2018.1807078

[7] Oakes, P., Loukas, M., Oskouian, R. J. and Tubbs, 2016 Oakes, P., Loukas, M., Oskouian, R. J. and Tubbs, R. S. (2016). The neuroanatomy of depression: A review. *Clinical Anatomy.*

[8] Richards, D. (2011). Prevalence and clinical course of depression: A review. *Clinical Psychology Review,* 31(7), 1117-1125. https://doi.org/10.1016/j.cpr.2011.07.004

[9] Krishnan, V., & Nestler, E. J. (2008). The Molecular Neurobiology of Depression. *Nature,* 455(7215), 894-902. https://doi.org/10.1038/nature07455

[10] Werner, F. M., & Coveñas, R. (2010). Classical Neurotransmitters and Neuropeptides Involved in Major Depression: A Review. *International Journal of Neuroscience,* 120(7), 455-470. DOI: https://doi.org/10.3109/00207454.2010.48365

[11] Alexander, L., Wood, C. M., Gaskin, P. L. R., Sawiak, S. J., Fryer, T. D., Hong, Y. T., McIver, L., Clarke, H. F., & Roberts, A. C. (2020). Over-activation of Primate Subgenual Cingulate Cortex Enhances the Cardiovascular, Behavioral and Neural Responses to Threat. *Nature Communications,* 11(1). DOI: https://doi.org/10.1038/241467-020-19167-0

[12] Rudebeck, P. H., Putnam, P. T., Daniels, T. E., Yang, T., Mitz, A. R., Rhodes, S. E. V., & Murray, E. A. (2014). A Role for Primate Subgenual Cingulate Cortex in Sustaining Autonomic Arousal. *Proceedings of the National Academy of Sciences of the United States of America,* 111(14), 5391-5396. DOI: https://doi.org/10.1073/pnas.1317695111.

[13] Drevets, W. C., Savitz, J., & Trimble, M. (2008). The Subgenual Anterior Cingulate Cortex in Mood Disorders. *CNS Spectrums,* 13(8), 663-681. DOI: https://doi.org/10.1017/S1092852900013754.

[14] Li, B. J., Friston, K., Mody, M., Wang, H. N., Lu, H. B., & Hu, D. W. (2018). A Brain Network Model for Depression: From Symptom Understanding to Disease Intervention. *CNS Neuroscience and Therapeutics,* 24(11), 1004-1019. DOI: https://doi.org/10.1111/cns.12998.

[15] Damoiseaux, J. S., Rombouts, S. A. R. B., Barkhof, F., Scheltens, P., Stam, C. J., Smith, S. M., & Beckmann, C. F. (2006). *Consistent Resting-State Networks.* 2.

[16] Liang, X., Zou, Q., He, Y., & Yang, Y. (2016). Topologically Reorganized Connectivity Architecture of Default-Mode, Executive-Control, and Salience Networks across Working Memory Task Loads. *Cerebral Cortex,* 26(4), 1501-1511. DOI: https://doi.org/10.1093/cercor/bhu316.

[17] Dichter, G. S., Gibbs, D., & Smoski, M. J. (2015). A systematic review of relations between resting-state functional-MRI and treatment response in major depressive disorder. *Journal of Affective Disorders,* 172, 8-17. DOI: https://doi.org/10.1016.j.jad.2014.09.028.

[18] U.S. Pat. No. 9,504,846 B2, Talebinejad, entitled "CIRCUIT AND METHOD FOR USE IN TRANSCRANIAL MAGNETIC STIMULATION";

[19] O'Reardon, J. P., Solvason, H. B., Janicak, P. G., Sampson, S., Isenberg, K. E., Nahas, Z., McDonald. W. M., Avery, D., Fitzgerald, P. B., Loo, C., Demitrack, M. A., George, M. S., Sackeim, H. A. (2007). Efficacy and Safety of Transcranial Magnetic Stimulation in the Acute Treatment of Major Depression: A Multisite Randomized Controlled Trial. *Biol Psychiatry,* 62 (11), 1208-16. DOI: https://doi.org/10.1016/j.biopsych.2007.01.018.

[20] Health Quality Ontario. (2016). Repetitive Transcranial Magnetic Stimulation for Treatment-Resistant Depression: A Systematic Review and Meta-Analysis of Randomized Controlled Trials. *Ont. Health Technol Assess Ser.,*16(5), 1-66. PMID: 27099642; PMCID: PMC4808719.

[21] Rush, A., Fava, M., Wisniewski, S., et al (2004). Sequenced Treatment Alternatives to Relieve Depression (STAR*D): Rationale and Design. *Controlled Clinical Trials* 25, 119-142.

It should be clear that various aspects of the present invention may be implemented as software modules in an overall software system, and that the stimulation device used to implement the present invention may be controlled by such software modules. As such, the present invention may thus take the form of computer executable instructions that, when executed, implement various software modules with predefined functions.

Embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g., "C" or "Go") or an object-oriented language (e.g., "C++", "java", "PHP", "PYTHON" or "C #"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A method for generating a pulse train using a device comprising a circuit, wherein said circuit comprises:

an energy source for delivering energy to said circuit and for recovering at least a portion of said energy from said circuit, said energy source having an adjustable voltage level;

at least one voltage control device for setting said voltage level of said energy source and controlling said voltage level once set; and a coil through which said energy is passed in a manner that passage of said energy creates a magnetic field around said coil, and wherein said coil is positioned near an individual's brain in a manner that said magnetic field thereby induces a current flow in said individual's brain;

and said method comprises the steps of:

(a) delivering said energy to said coil while said voltage level of said energy source is at a first level until said energy in said coil reaches a predetermined peak value;

(b) responsive to said energy in said coil reaching said predetermined peak value, using said voltage control device to change said voltage level from a first level to a second level;

(c) recovering a majority of said energy to said energy source while said voltage level is at said second level; and (d) repeating steps (a) to (c) until a predetermined number of pulses have been generated, said predetermined number of pulses comprising said pulse train;

wherein the intensity of each subsequent pulse in said pulse train is within ±5% of the intensity of a first pulse in said pulse train, wherein said first level is a voltage level that is at least 5 times greater than said second level, and wherein said pulse is unidirectional, monophasic, and triangular.

2. The method according to claim 1, wherein said at least one voltage control device comprises at least one semiconductor switching device.

3. The method according to claim 2, wherein said at least one semiconductor switching device is an insulated gate bipolar transistor (IGBT).

4. The method according to claim 2, wherein said at least one voltage control device further comprises at least one inductor.

5. The method according to claim 1, wherein said method is used to treat a neurological condition or a neurophysiological condition of said individual.

6. The method according to claim 1, wherein said energy source is an energy storage device for storing energy received from a power source.

7. The method according to claim 6, wherein said energy storage device is a capacitor.

8. The method according to claim 6, wherein said energy storage device is a capacitor bank.

* * * * *